United States Patent [19]

Llenado

[11] 4,157,978
[45] Jun. 12, 1979

[54] MODIFIED SILICATES

[75] Inventor: Ramon A. Llenado, West Chester, Ohio

[73] Assignee: The Procter & Gamble Company, Cincinnati, Ohio

[21] Appl. No.: 885,932

[22] Filed: Mar. 13, 1978

[51] Int. Cl.$^2$ .................... C07F 7/02; C11D 3/08; C11D 3/20; C11D 11/04

[52] U.S. Cl. ................... 252/135; 156/325; 252/27; 252/62; 252/89 R; 252/99; 252/109; 252/133; 252/140; 252/174; 252/179; 252/528; 252/547; 260/414; 260/429 R; 260/429.3; 260/429.5; 260/429.7; 260/429.9; 260/448 R; 260/448.2 B

[58] Field of Search ............ 260/429 R, 429.3, 429.5, 260/429.7, 429.9, 448 R, 448.2 B, 448.8 A, 414; 252/89, 99, 135, 133, 174

[56] References Cited

U.S. PATENT DOCUMENTS

| | | | |
|---|---|---|---|
| 3,130,071 | 4/1964 | Brockett | 260/429.5 X |
| 3,239,521 | 3/1966 | Weldes | 260/448.2 B |
| 3,461,146 | 8/1969 | Turner | 260/429.5 X |
| 3,657,149 | 4/1972 | Vandenberg | 260/429.7 X |
| 3,951,877 | 4/1976 | Okumura | 252/135 X |
| 3,962,132 | 6/1976 | Haschke | 252/430 |
| 4,040,972 | 8/1977 | Roebke | 252/179 |
| 4,073,735 | 2/1978 | Ramachandran | 252/8.8 |

FOREIGN PATENT DOCUMENTS

| | | | |
|---|---|---|---|
| 1028561 | 5/1966 | United Kingdom | 252/547 |
| 1041271 | 9/1966 | United Kingdom | 252/8.8 |
| 1213588 | 11/1970 | United Kingdom | 156/325 |
| 1343672 | 1/1974 | United Kingdom | 252/547 |

*Primary Examiner*—Dennis L. Albrecht
*Attorney, Agent, or Firm*—Robert B. Aylor; Richard C. Witte; Thomas H. O'Flaherty

[57] ABSTRACT

The compound

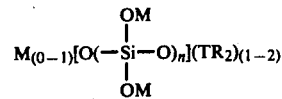

wherein each M is selected from the group consisting of Na, K, H and mixtures thereof; n is the degree of polymerization and ranges from about 2 to about 1,000; T is selected from the group consisting of Al, Ti, Zn, Zr, Sn, V, Mo, W, Se, Ge and mixtures thereof; and R is an acyl group containing from about 2 to about 30 carbon atoms and from about 0 to about 5 additional carboxylate groups; detergent compositions containing said compound and similar capped compounds; and processes for preparing said compound.

50 Claims, No Drawings

MODIFIED SILICATES

BACKGROUND OF THE INVENTION

Silicate compounds are very useful in formulating detergent compositions. They can act as detergency builders, corrosion inhibitors, structure formers, etc. However, it is well known that silicates have a tendency to polymerize when heated and cross-link when dehydrated and can cause detergent compositions to be too insoluble. There has been a continuing need for a silicate compound which would have the beneficial effects noted above, but would not have the tendency to polymerize and cross-link and form insoluble products. Lower ratio silicates, i.e., <2.0r although yielding more soluble detergent compositions cause those detergent compositions to cake, be hygroscopic, and to deteriorate with time upon moisture pick-up.

SUMMARY OF THE INVENTION

This invention relates to the discovery of novel compounds having the formula

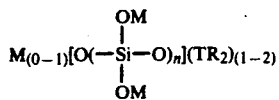

$$M_{(0-1)}[O(-\underset{\underset{OM}{|}}{\overset{\overset{OM}{|}}{Si}}-O)_n](TR_2)_{(1-2)}$$

wherein each M is selected from the group consisting of Na, K, H and mixtures thereof; n is the degree of polymerization and ranges from about 2 to about 1,000; T is selected from the group consisting of Al, Ti, Zn, Zr, Sn, V, Mo, W, Se, Ge and mixtures thereof; and R is an acyl group containing from about 2 to about 30 carbon atoms and from about 0 to about 5 additional carboxylate groups; detergent compositions containing said compounds and similar capped compounds; and processes for preparing said compound.

The above compounds are "capped" multimeric silicates which have a reduced tendency to further polymerization.

This invention also relates to detergent compositions containing from about 3% to about 50% of a detergent surfactant and from about 1% to about 40% of a capped, preferably low ratio (<2.0r), silicate; and from about 5% to about 95% of a detergency builder other than the said capped silicate.

This invention also relates to the process for producing said novel compounds in which an alkali metal, e.g., sodium or potassium, silicate having an SiO$_2$:M$_2$O ratio of less than 2 is reacted with a water soluble salt of T, preferably aluminum, titanium, zinc, zirconium, or tin salt or mixtures thereof in an aqueous medium in the presence of sufficient alkalinity to maintain the pH in a range of from about 9 to about 14 at a temperature of from about 10° C. to about 90° C. and, if the water soluble salt is not a water soluble carboxylate having an acyl radical R as defined hereinbefore, reacting the intermediate, e.g., aluminum, capped alkali metal silicate with a water soluble material that will provide a carboxylate ion R in aqueous solution.

DETAILED DESCRIPTION OF THE INVENTION

The Silicate Compound

Since the novel silicate compound is prepared from alkali metal silicates having an SiO$_2$:M$_2$O ratio below 2, the cation M and the degree of polymerization n will be determined by the original silicate. If in the original reaction both ends of the silicate are capped, no further polymerization is likely. However, if the silicate is only capped on one end, then, of course, dimers of the capped multimeric silicate can form. Typically the alkali metal will be sodium or potassium, preferably sodium, and about half of the M's will be hydrogens. The degree of polymerization normally is from about 2 to about 1,000; more desirably is from about 2 to about 50; and typically is about 20 on the average. The preferred T is aluminum or titanium, but most preferably aluminum.

The acyl group can be any of a very large number of acyl groups. Desirably, however, the acyl group will contain no more than about 6 carbon atoms, since it is normally desirable that the organic acyl group not detract from the inorganic character of the silicate. Examples of suitable preferred groups include acetates, lactates, tartrates, citrates, adipates, succinates, propionates, benzoates, mellitates, salicylates, laurates, tallowates, and mixtures thereof. The acetate and lactate groups are highly preferred. Normally the acetate group will be used since it is convenient, readily available, and relatively inexpensive and excess alkali metal acetates are useful in detergent compositions, especially spray dried detergent compositions, to act as moisture "sinks" by forming hydrates.

The silicate compound can be used anywhere the unmodified silicate is used, e.g., in forming adhesives, treating metals, preparing thick greases, forming insulation, and especially preparing detergent compositions. The novel capped silicate compound can be formed into particles, e.g., by spray drying which then can be shipped, stored and used as needed to form aqueous compositions readily.

The Process

The process for forming the preferred novel modified silicate compounds of this invention involves reacting an alkali metal silicate having an SiO$_2$:M$_2$O ratio of less than 2 with a water soluble salt of T, preferably aluminum, titanium, zinc, zirconium, or tin metal salt in aqueous solution, preferably after the water soluble metal salt has been fully dissolved. The temperature of the reaction should be kept low to avoid polymerizing the silicate prematurely. Although the reaction can take place at a wide variety of temperatures from about 10° C. to about 90° C., it is preferred that the reaction be carried out at a temperature of from about 55° C. to about 75° C. A convenient temperature is about 65° C.

The pH of the reaction mixture should be from about 9 to about 14, preferably from about 11 to about 13.5 and most preferably between about 12.5 and about 13 to promote the reaction and to minimize polymerization.

The source of the carboxylate ion can be either the water soluble salt of T, or any water soluble carboxylate; typically a sodium, potassium or ammonium or substituted ammonium carboxylate. If, for example, aluminum carboxylates are used, they should not be added to water too early or they may hydrolyze and form insoluble aluminum compounds. For some carboxylates such as the acetates and the lactates which function as hydratable moisture "sinks" it is desirable to add excess water soluble carboxylate. Such hydratable carboxylates should dehydrate at a lower temperature than the silicate.

Care must be taken to avoid adding any separate water-soluble carboxylate before the water-soluble metal salt to minimize premature hydration and gel formation.

As mentioned hereinbefore, the silicate reactant should have an $SiO_2:M_2O$ ratio of less than 2, preferably from about 1 to 1.9, most preferably from about 1.4 to 1.6.

The Detergent Composition

The detergent compositions of this invention are any of the art recognized detergent compositions which can contain a normal low ratio silicate. When the silicates described hereinbefore and other "capped" silicates as disclosed hereinafter are incorporated into detergent compositions, especially those which are formed by spray-drying, there is an overall improvement in the physical characteristics and rate of solubility of the resulting detergent compositions especially those which have been spray dried. Use of the capped silicates of this invention permits incorporating a higher level of low-ratio silicate without appreciably harming the dissolving characteristics of the detergent granule. The "capped" silicates make the granules firmer, more free-flowing, and/or less hygroscopic as compared to granules containing normal "non-capped" silicate.

Spray dried detergent granules, according to this invention, can be prepared using crutcher mixes which contain from about 10% to about 50%, preferably at least about 20% water. it is a major advantage of this invention that it permits the production of crutcher mixes which contain a very low level of water while remaining pumpable because the viscosity of the aqueous capped silicate solutions are less viscous than the corresponding normal silicate solutions. This permits the preparation of spray dried detergent granules using less hydratable salts and/or lower heat inputs. Another advantage of the detergent compositions of this invention is that they can be formed as spray dried detergent granules, or otherwise, containing many ingredients which would be incompatible with normal alkali metal silicates.

The following patents describe detergent compounds which are suitable for incorporation in the detergent compositions of this invention. U.S. Pat. No. 4,056,481, Tate (Nov. 1, 1977); U.S. Pat. No. 4,049,586, Collier (Sept. 20, 1977); U.S. Pat. No. 4,040,988, Vincent et al (Aug. 9, 1977); U.S. Pat. No. 4,035,257, Cherney (July 12, 1977); U.S. Pat. No. 4,033,718, Holcomb et al (July 5, 1977); U.S. Pat. No. 4,019,999, Ohren et al (Apr. 26, 1977); U.S. Pat. No. 4,019,998, Benson et al (Apr. 26, 1977); U.S. Pat. No. 4,000,094, Fleming et al (Dec. 28, 1976); U.S. Pat. No. 4,000,080, Bartolotia et al (Dec. 28, 1976); U.S. Pat. No. 3,992,314, Cherney (Nov. 16, 1976); U.S. Pat. No. 3,985,669, Krummel et al (Oct. 12, 1976); U.S. Pat. No. 3,983,078, Collins (Sept. 28, 1976); and U.S. Pat. No. 3,954,632, Gloss (May 4, 1976); all of said patents being incorporated herein by reference.

The silicates of this invention are especially desirable for solving the problem set forth in U.S. Pat. No. 3,985,669. The silicates of this invention, when used with the aluminosilicate detergency builders defined in U.S. Pat. No. 3,985,669, permit the inclusion of larger amounts of silicate, which is extremely desirable. If large amounts of normal silicates are combined with the aluminosilicate detergency builder in a spray dried granule, there is a pronounced tendency to form insoluble granules.

Additionally, detergent compositions utilizing the silicates of this invention are initially harder, firmer, and/or more free-flowing, and do not deteriorate over time compared to detergent compositions utilizing normal silicates.

Yet another advantage of this invention is that the capped silicates are compatible with cationic materials. Thus these silicates are desirable for incorporation into detergent compositions of the type disclosed in co-pending patent applications of J. R. Cockrell, Ser. No. 852,428 filed Nov. 17, 1977, now abandoned, and A. P. Murphey, Ser. No. 852,187 filed Nov. 16, 1977, said applications being incorporated herein by reference.

In addition to the specific novel capped silicate materials disclosed hereinbefore, detergent compositions of this invention can also be prepared using other capped silicate materials known in the art. Examples include those silicates having ratios of $SiO_2:M_2O$, where M is sodium or potassium, of from about 1 to about 4, in which $TR_2$ is replaced by—Si $R'_3$ in which each R' is selected from the group consisting of substituted alkyl, aryl and substituted groups containing from one to about 12, preferably no more than about 6 carbon atoms and the group contains a total of from 3 to about 16, preferably no more than about 18 carbon atoms. Such capped silicate materials can be prepared by using the corresponding silyl halide, preferably the chloride, as a reactant. Similar reactions have been used as part of analyses of silicate minerals in which the minerals were simultaneously acid leached and trimethyl silyl end-blocked to yield trimethylsilyl silicates which were characteristic of the mineral. See, e.g., Kirk-Othmer, Encyclopedia of Chemical Technology, 2nd Ed., Volume 18, pp. 260–267 and pp. 134–166 and references cited therein. All of the above references are incorporated herein by reference.

"Substituted" as used herein means that hydrogen atoms can be replaced by compatible groups such as hydroxy and carboxylate groups and the individual R' (or R or R" groups as hereinafter defined) can be joined to form ring structures and the chains can be interrupted by ether, ester, etc., groups.

Other capped silicates which can be used include the reaction product of 1.0r to 4.0r sodium or potassium silicates with water soluble or dispersible quaternary ammonium salts or hydroxides giving a capping group which replaces—$TR_2$ with—$N(R")_4$ in which each R" group is selected from the group consisting of substituted and unsubstituted alkyl, aryl, alkaryl, aralkyl, alkyl amido, amido alkyl, and ester and ether groups containing from one to about 30, preferably no more than about 18, carbon atoms and the total number of carbon atoms in said—$N(R")_4$ group being from 4 to about 120, preferably no more than about 40. Such "capped" silicates are described in British Pat. Nos. 1,028,561; 1,041,271; 1,213,588; and 1,343,672, said patents being incorporated herein by reference.

The invention can be better understood from the following examples which should not be considered as limiting.

EXAMPLE 1

A series of alkali metal silicates having varying indicated $SiO_2:M_2O$ ratios at a concentration of about 44% in water were reacted with aluminum sulfate at a concentration of about 1% at a temperature of about 30° C. and a pH of about 13. Initially there was a precipitation which was visibly worse for the higher silicate ratios.

However, in the case of 1.6 ratio silicate the coagulate or precipitate redissolved after about 5 minutes to form a clear solution. Higher ratio silicates (e.g., <2.0r) did not redissolve.

The above procedure was then repeated with the subsequent addition of sodium acetate. No appreciable coagulation or precipitation effects were observed for $SiO_2:M_2O$ ratios of <2.0r. The 1.6 ratio silicate product gave a clear solution with a viscosity only about half that of the original silicate. When the modified 1.6 ratio silicate was heated and dried the resulting material was soluble in water. When the dried modified 1.6 ratio silicate was stored at 80° F./60% relative humidity, the material was not hygroscopic and was dry and firm to the touch. In contrast when 1.6 ratio silicate itself was dried it was extremely hygroscopic and soft to the touch.

Several tests were performed to demonstrate that a modified silicate was synthesized.

The first test was a detergency test. In this test a standard detergent composition was modified by including the same amount of the indicated compounds in a standard composition having a formula as follows. Sodium $A_{14-16}E_3$ sulfate ($A_{14-16}$=an alkyl group consisting from about 14 to about 16 carbon atoms; $E_3$=a polyethylene glycol chain containing an average of about 6 carbon atoms)—15%; sodium $A_{16-18}$ sulfate—2%; hydrated sodium zeolite A having an average particle size of about 3 microns—25%; the indicated silicate—20%; sodium carbonate—10%; and water and minors—the balance.

| Composition | Silicate Component | Detergency Results in 7 gr. of hardness 100° F. |
|---|---|---|
| A | 2.0r silicate | Standard |
| B | 2.0r silicate + 1% aluminum sulfate replacing water | Significantly poorer |
| C | 1.6r silicate | Equal |
| D | 1.6r silicate + 1% aluminum sulfate | Poorer |
| E | 2.0r silicate + sodium acetate | Equal |
| F | 1.6r silicate + aluminum sulfate + 3% sodium acetate | Better |

The above results clearly indicate that the combination of 1.6r silicate reacted with aluminum salt and sodium acetate, as set forth hereinbefore, is clearly different and better than any of the other possible permutations or combinations.

In the second test, X-ray diffraction patterns were obtained to show that 1.6r silicate dried alone was amorphous to X-rays; that 1.6r silicate reacted with aluminum sulfate as set forth hereinbefore and dried was generally amorphous to X-ray and there was no trace of crystalline aluminum sulfate; and that 1.6r silicate+aluminum sulfate+sodium acetate reacted as hereinbefore and dried was partially crystalline but showed no evidence of aluminum sulfate, sodium acetate, aluminum acetate or sodium sulfate.

From the above X-ray data, the logical inference is that a silicate capped with aluminum diacetate radical has been formed and that the product of the process described herein has the generic formula set forth hereinbefore.

In the third test the viscosity was checked for the reaction product of 1.6r silicate+aluminum sulfate vs. 1.6r silicate alone and 1.6r silicate+aluminum sulfate+ sodium acetate as reacted hereinbefore. The total reaction product had a much lower viscosity than 1.6r silicate alone which in turn had a lower viscosity than the reaction product of 1.6r silicate and aluminum sulfate.

The inference from this test is that the capping with aluminum diacetate inhibits polymerization relative to the initial 1.6r silicate.

EXAMPLE II

Using a modified silicate as in Example I, detergent compositions as shown below were spray dried in a 10 ft. tower.

| | Compositions | | |
|---|---|---|---|
| | A | B | C |
| Sodium alkyl polyethoxylate [having 14 to 16 carbon atoms in the alkyl group and an average of 3 ethoxy groups ($A_{14-16}E_3$)] Sulfate | 15% | 15% | 14% |
| Sodium $A_{16-18}$ Sulfate | 2% | 2% | 2% |
| Hydrated Sodium Zeolite A having an average particle size of about 3 microns | 25% | 25% | 25% |
| Sodium Silicate (ratio) | 20% (2.0r) | 20% (1.6r) | 20% (1.6r) |
| Aluminum Sulfate Octadeca-Hydrate | 0% | 0% | 1% |
| Sodium Acetate | 0% | 0% | 3% |
| Sodium Carbonate | 10% | 10% | 5% |
| Water and Minors | 8% | 8% | 8% |

The above three compositions were tested for solubility using a test in which a 0.12% solution of the granular detergent is formed by adding the detergent granules to water and shaking for ten minutes. The resulting solution is then filtered through a black fabric (diameter of filtration zone equal 2 inches). Any insolubles retained on the black fabrics are graded using a visual scale in which a grade of 1 means complete coverage of the fabric by the insolubles and a grade of 10 means no insolubles can be seen. The results are given as a "Deposition Grade."

The extent of the deterioration of the physical characteristics of the granules with time is checked by storing granules packed one inch thick at a constant 80° F./10% relative humidity and 80° F./60% relative humidity and in a cycling room where the temperature and relative humidity change from 79° F./86% relative humidity to 93° F./52% relative humidity and the products are then tested for deposition grades to see if the deposition was worse after storage.

The compositions were also tested for their tendency to cake and the ease with which the granules could be poured from a container. For the caking test and the pourability test, grades are given based upon comparison with standard commercial products.

The results were as follows:

| | Compositions | | |
|---|---|---|---|
| | A | B | C |
| Deposition Grade | 5 | 6 | 7 |
| Deterioration with Time | Medium | High | No change |
| Caking Grade | Medium | Poor | Good |
| Pourability | Good | Poor | Good |

EXAMPLE III

When one is preparing a product according to Example I(A) it is not possible to prepare crutcher mixes containing less than about 30% water. However, it has been possible to prepare compositions according to Example II(C) with crutcher moistures as low as about 20%. For all such crutcher mixes containing capped silicates the viscosity is considerably lower in a range of crutcher moisture levels from about 10% to about 50%, resulting in a savings in pumping costs.

The above Example clearly indicates that the capped silicates of this invention are surprisingly effective in providing good granule characteristics even at reduced levels.

EXAMPLE V

Detergent compositions containing capped silicates prepared with varying amounts of aluminum sulfate and sodium acetate and additionally containing sodium sulfosuccinate were spray dried in a ten foot tower giving results as follows:

|  | Compositions | | | | |
| --- | --- | --- | --- | --- | --- |
|  | A | B | C | D | E |
| Sodium $C_{11.8}$ Alkyl Benzene Sulfonate | 12% | 12% | 12% | 12% | 12% |
| Sodium $A_{14-16}E_1$ | 6% | 6% | 6% | 6% | 6% |
| Hydrated Sodium Zeolite A having an average particle size of about 3 microns (Zeolite A) | 20% | 20% | 20% | 20% | 20% |
| Sodium Silicate (ratio) | 12%(2.0r) | 7%(1.6r) | 7%(1.6r) | 7%(1.6r) | 7%(1.6r) |
| Aluminum Sulfate Octadecahydrate | 0% | 0.1% | 0.1% | 0.3% | 0.3% |
| Sodium Sulfosuccinate | 2.0% | 2% | 0% | 2% | 0% |
| Sodium Carbonate | 5% | 13% | 13% | 13% | 13% |
| Sodium Acetate | 0% | 3% | 5% | 3% | 5% |
| Water and Minors | 6.5% | 4% | 4% | 4% | 4% |
| Deposition Grade | 5.5 | 8.5 | 8.5 | 8.5 | 9.0 |
| Deterioration with time | Yes | No | No | No | No |
| Pourability | Good | Good | Good | Good | Good |
| Caking under Storage | Yes | No | No | No | No |

EXAMPLE IV

Detergent compositions with varying levels of silicate, both normal and modified, were spray dried in a ten foot tower as follows:

The above Example shows that mixtures of carboxylates will work. Examples C and E were repeated with varying moisture levels from 3% to 8% by weight of finished product and substantially equivalent results were obtained with the above tests.

|  | Compositions | | | | |
| --- | --- | --- | --- | --- | --- |
|  | A | B | C | D | E |
| Sodium $C_{11.8}$ (containing an average of 11.8 carbon atoms) Benzene Sulfonate | 12% | 12% | 12% | 12% | 12% |
| Sodium $A_{14-16}E_1$ Sulfate | 6% | 6% | 6% | 6% | 6% |
| Hydrated Sodium Zeolite A having an average particle size of about 3 microns | 20% | 20% | 20% | 20% | 20% |
| Sodium Silicate (ratio) | 12%(2.0r) | 15%(1.6r) | 10%(1.6r) | 7%(1.6r) | 7%(1.6r) |
| Aluminum Sulfate Octadecahydrate | 0% | 0.1% | 0.1% | 0.1% | 0.05% |
| Sodium Acetate | 0% | 5% | 5% | 5% | 5% |
| Sodium Carbonate | 5% | 10% | 10% | 10% | 10% |
| Water and Minors | 6.5% | 4% | 4% | 4% | 4% |
| Deposition Grades | 5.5 | 8.5 | 8.5 | 8.5 | 8.5 |
| Deterioration with time | Yes | No | No | No | No |
| Pourability | Good | Good | Good | Good | Good |
| Caking under Storage | Yes | Slightly | No | No | No |

EXAMPLE VI

The capped silicate of Example I was tested for magnesium ion sequestration using a divalent ion selective electrode. Results indicate that magnesium ions are tied up even when silicates are capped and at a faster rate than when "uncapped" silicates are used. The magnesium ion was initially present at a level of about 4.0 gr./gal. and the silicate was at a level of 200 ppm. Both capped and uncapped silicate reduced the magnesium ion concentration to between 0.04 and 0.4 gr./gal. within a minute after addition of the silicate. The pH of the capped silicate during the test was about 10.8.

EXAMPLE VII

Using the modified silicate of Example I detergent compositions, as shown below, were spray dried in a 10 ft. tower.

|  | Compositions | | |
| --- | --- | --- | --- |
|  | A | B | C |
| Sodium $C_{11.8}$ Alkyl Benzene Sulfonate | 12 | 12 | 12 |
| Sodium $A_{14-16} E_1$ Sulfate | 6 | 6 | 6 |
| Sodium Silicate (ratio) | 12(2.0) | 7(1.6) | 7(1.6) |
| $Al_2(SO_4)_3 \cdot 18 H_2O$ | — | — | 0.3 |
| Na Acetate | — | — | 1.0 |
| Sodium tripolyphosphate | 21 | 21 | 21 |
| Sodium Sulfate | 24 | 24 | 24 |
| Water and Minors | Balance | Balance | Balance |
| Results |  |  |  |
| Deposition Grade | 6.0 | 9.0 | 9.0 |
| Deterioration with time | Yes | Yes | No |
| Pourability | Good | Poor | Good |
| Caking under storage | Good | Poor | Good |

The above results show that phosphate formulas also benefit from capped silicate. Example C was repeated with 12 parts 1.6 ratio silicate and 2 parts Na acetate and dried to from 2.5% to 10% by weight water on a finished product basis and substantially equivalent results were obtained with the above tests.

EXAMPLE VIII

1.6r vs. 2.0r Silicate

Viscosity Comparison

The following are viscosities in CPS of the indicated materials at 25° C.

|  | Viscosity (CPS) | |
| --- | --- | --- |
|  | 2.0r | 1.6r |
| Stock silicate (44% Solids in water) | 269 | 193 |
| Effect of $Al_2(SO_4)_3 \cdot 18 H_2O$ | | |
| 20 pts. silicate  1.0 pt $Al_2(SO_4)_3 \cdot 18 H_2O$ | 244 | 135 |
| 20 pts silicate  0.5 pt $Al_2(SO_4)_3 \cdot 18 H_2O$ | 193 | 141 |
| 20 pts silicate  0.25 pt $Al_2(SO_4)_3 \cdot 18 H_2O$ | 235 | 183 |
| Effect of Sodium Acetate | | |
| 20 pts silicate  3.0 pts sodium acetate | 252 | 175 |
| Effect of $Al_2(SO_4)_3 \cdot 18 H_2O$ + Sodium Acetate | | |
| 20 pts silicate  3.0 pts sodium acetate | | |
| + 1.0 $Al_2(SO_4)_3 \cdot 18 H_2O$ | 285 | 147 |
| + 0.5 $Al_2(SO_4)_3 \cdot 18 H_2O$ | 245 | 158 |
| + 0.25 $Al_2(SO_4)_3 \cdot 18 H_2O$ | 244 | 144 |
| Effect of Zeolite A detergency builder | | |
| 20 pts silicate  + 5 pts hydrated sodium zeolite A  average particle size ~3µ(zeolite A | 459 | 267 |
| + 25 pts zeolite A | 3,888 | 1,468 |
| Effect of "detergent formula" (surfactant mixture of Example II A) | | |
| 20 pts silicate  + 16 pts detergent formula | 15,244 | 7,784 |
| Effect of detergent formula and Zeolite A | | |
| 20 pts silicate  + 16 pts detergent formula  + 25 pts Zeolite A | 9,408 | 6,060 |
| Effect of "capped" silicate | | |
| 20 pts silicate  + 0.25 $Al_2(SO_4)_3 \cdot 18 H_2O$  + 3 pts sodium acetate  + 16 pts detergent formula | 6,056 | 3,896 |
| 20 pts silicate  + 0.25 $Al_2(SO_4)_3 \cdot 18 H_2O$  + 3 pts sodium acetate  + 16 pts detergent formula  + 25 pts Zeolite A | 6,240 | 4,292 |

As can be seen, although capped 2.0r silicate appears slightly better than uncapped, the 1.6r silicate is clearly superior.

When, in the above examples, the following salts are used to replace the aluminum sulfate on an equivalent basis substantially similar results are obtained in that the "capped" silicates are formed, the crutcher mixes have a lowered viscosity, the resulting granules have desirably improved physical and dissolving characteristics as compared to similar compositions in which the silicates are not capped and magnesium control is obtained:

Aluminum fluoride, aluminum chloride, aluminum bromide, aluminum iodide, aluminum hydroxide, aluminum sulfide, aluminum sulfate, aluminum sulfate, aluminum nitrite, aluminum nitrate, aluminum phosphate, aluminum carbonate, aluminum borate, the corresponding titanium, ziconium, zinc, tin, vanadium, molybdenum, tungsten, selenium, and germanium salts and mixtures thereof in e.g. a 1:1 molar ratio.

When, in the above examples, the following carboxylate salts are substituted for the sodium acetate on, e.g., an equivalent basis, substantially equivalent results are obtained in that the resulting crutcher mixes have lower viscosities and the resulting granules have good physical characteristics and dissolving characteristics as compared to similar compositions in which the silicates are not capped and magnesium control is obtained:

The sodium potassium, ammonium, monoethanol ammonium, diethanol ammonium, triethanol ammonium and tetramethyl ammonium salts of the following acids and mixtures thereof on, e.g., a 5.1 ratio by weight formic, propionic, butyric, iso-butyric, n-valeric, caproic, enanthic, caprylic, pelargonic, glycolic, lactic, acrylic, oxalic, malonic, succinic, glutaric, adipic, pimelic, suberic, azelaic, sebacic, tartaric, maleic, fumaric, malic, benzoic, phthalic, isophthalic, terepthalic, salicyclic, anthramilic, cinnamic, mandelic, citric, mellitic, and adipic acids and mixtures thereof in e.g. 1:1 ratios.

When, in the above examples, the following surfactant detergents are substituted on an equal weight basis for the specific surfactant detergents, substantially equivalent results are obtained in that the resulting crutcher mixes have lower viscosities and the resulting granules have better physical characteristics and dissolving characteristics than similar compositions in which the silicates are not capped: sodium or potassium tallow alkyl sulfate; sodium or potassium coconut alkyl glyceryl ether sulfonate; sodium or potassium $C_{15}$ alkyl phenol polyethoxylate (3) sulfate; coconut fatty alcohol polyethoxylate (5); tallow fatty alchol polyethoxylate (9); s-$C_{14-15}$ alcohol polyethoxylate (4); $C_{12-13}$ alcohol polyethoxylate (5); $C_{12}$ alkylphenol polyethoxylate (8); coconut alkyl dimethylamine oxide; 3-(N,N-dimethyl-N-coconut alkyl ammonio)-propane-1-sulfonate; 3-(N,N-dimethyl-N-coconut alkylammonio)-2-hydroxypropane-1-sulfonate; sodium or potassium coconut soap; sodium or potassium tallow soap; coconut trimethylammonium chloride; and sodium or potassium $C_{14-18}$ paraffin sulfonate, and mixtures thereof in, e.g., 1:1 ratios.

When in the above compositions, the following builder materials are substituted either wholly or in part for the hydrated zeolite A and/or the sodium carbonate on an equal weight basis substantially equivalent results are obtained in that the resulting crutcher mixes have lower viscosities, and the resulting granules have better physical characteristics and dissolving characteristics than similar compositions in which the silicate is not capped: sodium or potassium tripolyphosphate, sodium or potassium pyrophosphate; sodium or potassium carboxymethyloxysuccinate; sodium or potassium citrate; sodium, potassium, ammonium, triethanolammonium, monoethanolammonium, or diethanolammonium carboxymethyloxymalonate; and sodium or potassium hexametaphosphate and e.g., 1:1 mixtures thereof.

When, in the above Examples, the following capped silicates are substituted for the aluminum diacetate capped silicate, substantially equivalent results are obtained in the resulting crutcher mixes have lower viscosities, and the resulting granules have better physical and dissolving characteristics than similar compositions that in which the silicates are not capped: trimethylsiyl capped 1.6r, 2.0r, 3.2r or 4.0r sodium or potassium silicate; methyl ditallow alkyl silyl capped 1.6r, 2.0r, 3.2r or 4.0r silicate; ditallowalkyl dimethylammonium partial salts of 1.6r, 2.0r, 3.2r, or 4.0r sodium or potassium silicate having an average of one or two molecules of the ammonium cation per molecule of silicate multimer; tetramethylammonium partial salts of 1.6r, 2.0r, 3.2r or 4.0r sodium or potassium silicates having 1, 2, or 4 moles of the ammonium cation per mole of silicate multimer; coconut alkyl dimethylammonium partial salt of 2.8r sodium silicate having 2 moles of ammonium catio per mole of silicate multimer; or the examples of British Pat. Nos. 1,028,361 and 1,343,672 and 1,213,588 and, e.g., 1:1 mixtures thereof.

All percentages, ratios and parts are by weight unless otherwise specified.

What is claimed is:

1. The compound

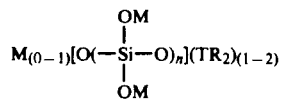

wherein each M is selected from the group consisting of Na, K, H and mixtures thereof; n is the degree of polymerization and ranges from about 2 to about 1,000; T is selected from the group consisting of Al, Ti, Zn, Zr, Sn, V, Mo, W, Se, Ge and mixtures thereof, R is an acyl group containing from about 2 to about 30 carbon atoms and from 0 to about 5 additional carboxylate groups.

2. The compound of claim 1 wherein T is selected from the group consisting of Al, Ti, Zn, Zr, Sn and mixtures thereof.
3. The compound of claim 2 wherein M is sodium.
4. The compound of claim 3 wherein n is from about 2 to about 50.
5. The compound of claim 4 wherein T is aluminum.
6. The compound of claim 5 wherein R contains up to about 6 carbon atoms.
7. The compound of claim 6 wherein each R is selected from the group consisting of acetate, tartrate, citrate, lactate, adipate, succinate, propionate and mixtures thereof.
8. The compound of claim 7 wherein each R is selected from the group consisting of acetate and lactate.
9. The compound of claim 8 wherein R is acetate.
10. The compound of claim 8 wherein R is lactate.
11. The compound of claim 1 wherein T is aluminum.
12. The compound of claim 11 wherein each R is selected from the group consisting of acetate, tartrate, citrate, lactate, adipate, succinate, propionate and mixtures thereof.
13. The compound of claim 12 wherein each R is selected from the group consisting of acetate and lactate.
14. The compound of claim 12 wherein R is acetate.
15. The compound of claim 12 wherein R is lactate.
16. The compound of claim 1 wherein T is zinc.
17. The compound of claim 16 wherein n is from about 2 to about 50.
18. The compound of claim 1 wherein T is titanium.
19. The compound of claim 18 wherein n is from about 2 to about 50.
20. A spray dried detergent composition containing from about 3% to about 50% of a detergent surfactant; from about 1% to about 40% of a capped alkali metal silicate; and from about 5% to about 96% of a detergency builder other than said capped silicate wherein said capped silicate has the formula

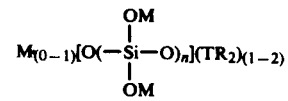

wherein each M is selected from the group consisting of Na, K, H and mixtures thereof; n is the degree of polymerization and ranges from about 2 to about 1,000; T is selected from the group consisting of Al, Ti, Zn, Zr, Sn and mixtures thereof, R is an acyl group containing from about 2 to about 30 carbon atoms and from 0 to about 5 additional carboxylic groups.

21. The composition of claim 20 wherein M is sodium.
22. The composition of claim 21 wherein n is from about 2 to about 50.
23. The composition of claim 22 wherein T is aluminum.
24. The composition of claim 23 wherein R contains up to about 6 carbon atoms.
25. The composition of claim 24 wherein each R is selected from the group consisting of acetate, tartrate, citrate, lactate, adipate, succinate, propionate and mixtures thereof.

26. The composition of claim 25 wherein each R is selected from the group consisting of acetate and lactate.

27. The composition of claim 26 wherein R is acetate.

28. The composition of claim 27 wherein R is lactate.

29. The composition of claim 20 wherein T is aluminum.

30. The composition of claim 29 wherein R contains up to about 6 carbon atoms.

31. The composition of claim 30 wherein each R is selected from the group consisting of acetate, tartrate, citrate, lactate, adipate, succinate, propionate and mixtures thereof.

32. The composition of claim 31 wherein each R is selected from the group consisting of acetate and lactate.

33. The composition of claim 31 wherein R is acetate.

34. The composition of claim 31 wherein R is lactate.

35. The composition of claim 20 wherein T is zinc.

36. The composition of claim 35 wherein n is from about 2 to about 50.

37. The composition of claim 20 wherein T is titanium.

38. The composition of claim 37 wherein n is from about 2 to about 50.

39. The composition of claim 20 containing from about 10% to about 28% of a detergent surfactant; from about 3% to about 25% of a capped alkali metal silicate; and from about 10% to about 85% of a detergency builder other than said capped silicate.

40. The process of preparing the detergent composition of claim 20 in which the detergent composition's components are mixed with from about 10% to about 50% water in a detergent crutcher and spray dried to form detergent granules.

41. The process of preparing the detergent composition of claim 20 in which the detergent composition's components are mixed with from about 20% to about 40% water in a detergent crutcher and spray dried to form detergent granules.

42. The process of preparing the detergent composition of claim 39 in which the detergent composition's components are mixed with from about 20% to about 30% water in a detergent crutcher and spray dried to form detergent granules.

43. The process for making the compound of claim 1 comprising reacting an alkali metal silicate having an $SiO_2:M_2O$ ratio of less than 2 with a water soluble salt selected from the group consisting of Al, Ti, Zn, Zr, Sn, V, Mo, W, Se, and Ge salts and mixtures thereof in an aqueous solution at a temperature of from about 10° C. to about 90° C. and a pH of from about 9 to about 14, and, where said water soluble salt does not provide carboxylate radical R, reacting the intermediate product with a water soluble carboxylate providing the ion R in aqueous solution.

44. The process of claim 43 wherein said alkali metal silicate is a sodium silicate.

45. The process of claim 44 wherein said temperature is from about 55° C. to about 75° C.

46. The process of claim 45 wherein said pH is from about 11 to about 13.5.

47. The process of claim 45 wherein the $SiO_2:M_2O$ ratio of said silicate is from about 1 to about 1.9.

48. The process of claim 47 wherein the ratio of said silicate is from about 1.4 to about 1.6.

49. The process of claim 44 wherein the pH is from about 11 to about 13.5.

50. The process of claim 48 wherein the $SiO_2:M_2O$ ratio of said silicate is from about 1 to about 1.9.

* * * * *